(12) United States Patent
Baxter et al.

(10) Patent No.: US 6,506,764 B1
(45) Date of Patent: Jan. 14, 2003

(54) HYDROXAMIC AND CARBOXYLIC ACID DERIVATIVES

(75) Inventors: Andrew Douglas Baxter, Cambridge (GB); David Alan Owen, Cambridge (GB); Duncan Hannah, Cambridge (GB); John Gary Montana, Cambridge (GB)

(73) Assignee: Darwin Discovery, Ltd. (GB)

( * ) Notice: Subject to any disclaimer, the term of this patent is extended or adjusted under 35 U.S.C. 154(b) by 0 days.

(21) Appl. No.: 09/623,669

(22) PCT Filed: May 12, 2000

(86) PCT No.: PCT/GB00/01804

§ 371 (c)(1),
(2), (4) Date: Sep. 6, 2000

(87) PCT Pub. No.: WO00/69822

PCT Pub. Date: Nov. 23, 2000

(30) Foreign Application Priority Data

May 12, 1999 (GB) .............................................. 9911075

(51) Int. Cl.[7] ..................... A61K 31/438; A61K 31/445; C07D 211/96; C07D 211/20; A61P 29/00; A61P 11/00

(52) U.S. Cl. ........................ 514/278; 514/331; 514/317; 514/534; 514/575; 546/16; 546/232; 546/237; 546/238; 560/12; 562/621

(58) Field of Search ........................... 546/16, 232, 237, 546/238; 514/278, 331, 317

(56) References Cited

U.S. PATENT DOCUMENTS 6,118,001 A * 9/2000 Owen .......................... 546/229
6,187,924 B1 * 2/2001 Owen .......................... 544/374

FOREIGN PATENT DOCUMENTS

WO           9805635           2/1998

\* cited by examiner

*Primary Examiner*—Evelyn Huang
(74) *Attorney, Agent, or Firm*—Saliwanchik, Lloyd & Saliwanchik

(57) ABSTRACT

Compounds of the formula

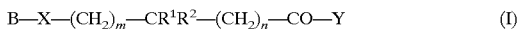

B—X—$(CH_2)_m$—$CR^1R^2$—$(CH_2)_n$—CO—Y    (I)

have therapeutic utility as inhibitors of metalloproteinases etc.

8 Claims, No Drawings

HYDROXAMIC AND CARBOXYLIC ACID DERIVATIVES

This application is a 371 of PCT /GB00/01804, filed on Jun. 12, 2000.

FIELD OF THE INVENTION

This invention relates to hydroxamic and carboxylic acid derivatives, and to their use in medicine.

BACKGROUND TO THE INVENTION

Metalloproteinases, including matrix metalloproteinase (MMP), (human fibroblast) collagenase, gelatinase and TNFα convertase (TACE), and their modes of action, and also inhibitors thereof and their clinical effects, are described in WO-A-9611209, WO-A-9712902 and WO-A-9719075, the contents of which are incorporated herein by reference. MMP inhibitors may also be useful in the inhibition of other mammalian metalloproteinases such as the ADAM or ADAM-TS families. Members of the ADAM family include TNFα convertase (TACE) and ADAM-10, which can cause the release of TNFα from cells, and others, which have been demonstrated to be expressed by human articular cartilage cells and also involved in the destruction of myelin basic protein, a phenomenon associated with multiple sclerosis.

Compounds which have the property of inhibiting the action of metalloproteinases involved in connective tissue breakdown, such as collagenase, stromelysin and gelatinase, have been shown to inhibit the release of TNFα both in vitro and in vivo. See Gearing et al(1994), Nature 370:555–557; McGeehan et al (1994), Nature370:558–561; GB-A-2268934; and WO-A-9320047. All of these reported inhibitors contain a hydroxamic acid zinc-binding group, as do the imidazole-substituted compounds disclosed in WO-A-9523790. Other compounds that inhibit MMP and/or TNFα are described in WO-A-9513289, WO-A-9611209, WO-A-96035687, WO-A-96035711, WO-A-96035712 and WO-A-96035714.

SUMMARY OF THE INVENTION

The invention encompasses novel compounds of formula (I) which are useful inhibitors of matrix metalloproteinases, ADAM or ADAM-TS enzymes, and which are useful for the treatment of diseases indicated by those enzymes and also and/or TNFα-mediated diseases, including degenerative diseases and certain cancers.

Novel compounds according to the invention are of the general type represented by formula (I):

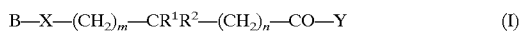

wherein m and n are each independently 0–2;

X is $S(O)_{1-2}$;

Y is OH or NHOH;

$R_1$ is H, $R^x$ or a group (optionally substituted with $R^x$) selected from $C_{1-6}$ alkyl, $C_{2-6}$ alkenyl, $C_{2-6}$ alkenyl, aryl, $C_{1-6}$ alkyl-aryl, heteroaryl, $C_{1-6}$ alkyl-heteroaryl, cycloalkyl, $C_{1-6}$ alkyl-cycloalkyl, heterocycloalkyl and $C_{1-6}$ alkyl-heterocycloalkyl; and $R^2$ is H or $C_{1-6}$ alkyl; or $CR_1R^2$ is cycloalkyl or heterocycloalkyl optionally substituted with $R^x$;

$R^x$ is $R^3$ or a group (optionally substituted with $R^3$) selected from $C_{1-6}$ alkyl, aryl, $C_{1-6}$ alkyl-aryl, heteroaryl and $C_{1-6}$ alkyl-heteroaryl;

$R^3$ is $OR^7$, $OCF_3$, $OCH_2F$, $OCHF_2$, $COR^7$, $CO_2R^4$, $CON(R_7)_2$, $N(R^7)_2$ $NR^7COR^7$, $NR^7CON(R^7)_2$, $NR^7CO_2R^8$, $NR^7SO_2R^8$, $S(O)_{0-2}R^8$, $SO_2N(R^7)_2$, cycloimidyl (optionally substituted with $R^5$) or, where $R^3$ is not attached to an aryl or heteroaryl group, $R^3$ may also be $=O$, $=NOR^{10}$ or $=NOH$;

$R^4$ is H or $C_{1-6}$ alkyl;

$R^5$ is $C_{1-6}$ alkyl;

B is cycloalkyl or cycloalkenyl substituted with a group selected from $=O$, $=NOR^7$ and $=CR^6R^7$, B is heterocycloalkyl or heterocycloalkenyl substituted with $=CR^6R^7$, or B is a spirocyclic system optionally substituted by $R^3$ or $R^7$;

$R^6$ is H or $C_{1-6}$ alkyl;

$R^7$ is H or a group selected from $C_{1-6}$ alkyl, aryl, $C_{1-6}$ alkyl-aryl, heteroaryl, $C_{1-6}$ alkyl-heteroaryl, cycloalkyl, $C_{1-6}$ alkyl-cycloalkyl, heterocycloalkyl and $C_{1-6}$ alkyl-heterocycloalkyl, wherein said group is optionally substituted with $R^8$, $COR^8$, $SO_{0-2}R^8$, $CO_2R^8$, $OR^8$, $OCF_3$, $OCH_2F$, $OCHF_2$, $CONR^4R^8$, $NR^6R^8$, or $SO_2NR^4R^8$ and for each case of $N(R^7)_2$ the $R^7$ groups are the same or different, or $N(R^7)_2$ is heterocycloalkyl optionally substituted with $R^8$, $COR^8$, $SO_{0-2}R^8$, $CO_2R^8$, $OR^8$, $CONR^4R^8$, $NR^4R^8$, or $SO_2NR^4R^8$; and $R^8$ is $C_{1-6}$ alkyl, aryl, $C_{1-6}$ alkyl-aryl, heteroaryl or $C_{1-6}$ alkyl-heteroaryl;

and the salts, solvates, hydrates, N-oxides, protected amino, protected carboxy and protected hydroxamic acid derivatives thereof.

DESCRIPTION OF THE INVENTION

Preferred compounds of the invention are those wherein one or more of the following apply: Y is NHOH; m+n=1; or X is $SO_2$. When X is $SO_2$, B is preferably heterocycloalkyl or heterocycloalkenyl bound through N to X.

It will be appreciated that the compounds according to the invention can contain one or more asymmetrically substituted carbon atoms. The presence of one or more of these asymmetric centers in a compound of formula (I) can give rise to stereoisomers, and in each case the invention is to be understood to extend to all such stereoisomers, including enantiomers and diastereomers, and mixtures including racemic mixtures thereof It will further be appreciated that the compounds according to the invention may contain an oxime and/or an alkene. These groups can give rise to geometrical isomers, and in each case the invention is to be understood to extend to all such isomers and mixtures thereof.

As used in this specification, alone or in combination, the term "$C_{1-6}$ alkyl" refers to straight or branched chain alkyl moiety having from one to six carbon atoms, including for example, methyl, ethyl, propyl, isopropyl, butyl, tert-butyl, pentyl, hexyl and the like.

The term "$C_{1-8}$ alkyl" refers to straight or branched chain alkyl moiety having from one to eight carbon atoms, including for example, methyl, ethyl, propyl, isopropyl, butyl, tert-butyl, pentyl, hexyl, octyl and the like.

The term "$C_{2-6}$ alkenyl" refers to a straight or branched chain alkyl moiety having two to six carbon atoms and having in addition one double bond, of either E or Z stereochemistry where applicable. This term would include for example, vinyl, 1-propenyl, 1- and 2-butenyl, 2-methyl-2-propenyl etc.

The term "$C_{2-6}$ alkenyl" refers to a straight or branched chain alkyl moiety having two to six carbon atoms and having in addition one triple bond. This term would include for example, ethynyl, 1-propynyl, 1- and 2-butynyl, 1-methyl-2-butynyl etc.

The term "cycloalkyl" refers to a saturated alicyclic moiety having from three to six carbon atoms and includes for example cyclopropyl, cyclobutyl, cyclopentyl, cyclohexyl and the like.

The term "cycloalkenyl" refers to an alicyclic moiety having from three to six carbon atoms and having in addition one double bond. This term includes, for example, cyclopentenyl and cyclohexenyl.

The term "heterocycloalkyl" refers to a saturated heterocyclic moiety having from two to six carbon atoms and one or more heteroatom from the group N, O, S (or oxidised versions thereof) which may be optionally benzofused at any available position. This includes for example azetidinyl, pyrrolidinyl, tetrahydrofuranyl, piperidinyl, benzodioxole and the like.

The term "heterocycloalkenyl" refers to an alicyclic moiety having from three to six carbon atoms and one or more heteroatoms chosen from the group N, O, S and having in addition one double bond. This term includes, for example, dihydropyranyl.

The term "aryl" refers to an aromatic carbocyclic radical having a single ring or two condensed rings, optionally substituted with an aryl group substituent. This term includes, for example phenyl or naphthyl.

The term "heteroaryl" refers to aromatic ring systems of five to ten atoms of which at least one atom is selected from O, N and S, and optionally substituted with an aryl group substituent. This term includes for example furanyl, thiophenyl, pyridyl, indolyl, quinolyl and the like.

The term "spirocyclic system" refers to a bicyclic system of which the two rings have a single common carbon atom and in which each ring is as defined above for cycloalkyl, cycloalkenyl, heterocycloalkyl or heterocycloalkenyl. Thus, each ring has 3 to 6 atoms which may all be C atoms or which may include one or more heteroatoms selected from N, O and S. Any unsaturation may be in either ring. This term includes, for example, spiro[4.5]decanyl.

The term "aryl group substituent" refers to a substituent chosen from halogen, CN, $CF_3$, $CHF_2$, $CH_2F$, and $NO_2$.

The term "halogen" means fluorine, chlorine, bromine or iodine.

The term "benzofused" refers to the addition of a benzene ring sharing a common bond with the defined ring system.

The term "cycloimidyl" refers to a saturated ring of five to ten atoms containing the atom sequence —C(=O)NC(=O)—. The ring may be optionally benzofused at any available position. Examples include succinimidoyl, phthalimidoyl and hydantoinyl.

The term "optionally substituted" means optionally substituted with one or more of the groups specified, at any available position or positions.

The terms "protected amino", "protected carboxy" and "protected hydroxamic acid" mean amino, carboxy and hydroxamic acid groups which can be protected in a manner familiar to those skilled in the art. For example, an amino group can be protected by a benzyloxycarbonyl, tert-butoxycarbonyl, acetyl or like group, or may be in the form of a phthalimido or like group. A carboxyl group can be protected in the form of a readily-cleavable ester such as the methyl, ethyl, benzyl or tert-butyl ester. A hydroxamic acid may be protected as either N or O-substituted derivatives, such as O-benzyl or O-tert-butyldimethylsilyl.

Salts of compounds of formula (I) include pharmaceutically-acceptable salts, for example acid addition salts derived from inorganic or organic acids, such as hydrochlorides, hydrobromides, p-toluenesulphonates, phosphates, sulphates, perchiorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically-labile ester of formula $CO_2R^9$ where $R^9$ may be an ethyl, benzyl, phenethyl, phenylpropyl, α or β-naphthyl, 2,4-dimethylphenyl, 4-tert-butylphenyl, 2,2,2-trifluoroethyl, 1-(benzyloxy)benzyl, 1-(benzyloxy,)ethyl, 2-methyl-1-propionyloxypropyl, 2,4,6-trimethylbenzyloxymethyl or pivaloylmethyl group.

Compounds of the general formula (I) may be prepared by any suitable method known in the art and/or by the following processes.

It will be appreciated that, where a particular stereoisomer of formula (I) is required, the synthetic processes described herein may be used with the appropriate homochiral starting material and/or isomers maybe resolved from mixtures using conventional separation techniques (e.g. HPLC).

The compounds according to the invention may be prepared by the following process. In the description and formulae below the groups $R^1$, $R^2$, $R^3$, $R^4$, $R^5$, $R^6$, $R^7$, $R^8$, $R^9$, B, X and Y are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see Greene et al, "Protective Groups in Organic Synthesis", Wiley Interscience.

A process for preparing compounds of general formula (I) comprises reacting a compound of formula B-SH (II) with (a) an alkylating agent of formula Z—$(CH_2)_n$—$CR^1R^2$—$(CH_2)_m$—COY (III) (wherein Z represents a suitable leaving group e.g. a halogen such as bromine, or an alkylsulfonate ester such as methanesulfonate), or (b) (when $R^2$=H) an acrylate of formula $CH_2$=$CR^1$—COY (IV) or (c) (when m+n=1 or 2) a lactone of the formula (V)

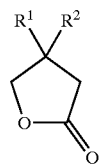

Alkylating agents of formula (III) can be obtained in chiral or racemic form. Many of these derivatives can be readily obtained from commercially available starting materials using methods known to those skilled in the art (e.g. see WO-9005719).

Compounds of formula (IV) may be prepared by the Mannich reaction (i.e. with paraformaldehyde and piperidine in a suitable organic solvent, such as 1,4-dioxane) on a dicarboxylic acid of general formula $HO_2C-CHR^1-CO_2H$ (VI). This reaction involves an eliminative decarboxylation step, resulting in the formation of an α,β-unsaturated carboxylic acid (i.e. where Y=OH) directly. Dicarboxylic acids of formula (VII) may be prepared by the alkylation of, for instance, diethyl malonate with an. alkylating agent of formula $R^1-Z$ (VIII), wherein Z is as defined above, followed by hydrolysis under basic conditions. Many alkylating agents of general formula (VIII) are available commercially or may be prepared from materials available commercially by methods known to those skilled in the art.

Lactones of formula (V) may be prepared by chemistry known to those skilled in the art. For example, see EP-A-780386.

Many compounds of formula (II) are available commercially, or may be prepared by standard aromatic, heteroaromatic or other chemistry known to those skilled in the art, from materials available commercially. Compounds of formula (II) can be prepared alternatively from compounds of the form B-Z (IX) by standard methods (for example, see WO-A-9611209). Many compounds of formula (IX) are available commercially.

Compounds of formula (I) in which B represents heterocycloalkyl attached to X through a nitrogen atom, and X represents $SO_2$, may be prepared by reacting an amine of formula B (X) with a sulphonyl chloride of formula $Cl-SO_2-(CH_2)_m-CR^1R^2-(CH_2)_n-CO-Y$ (XI). Such a reaction may be carried out using any standard conditions known to those skilled in the art, for example using procedures described in WO-A-9805635. Amines of formula B (X) may be prepared using any standard conditions known to those skilled in the art. Sulphonyl chlorides of formula (XI) have been previously described (WO-A-9805635 and WO-A-9924399).

Compounds of formula (I) may also be prepared by interconversion of other compounds of formula (I). Hydroxamic acids (Y=NHOH) of general formula (I) may be prepared from carboxylic acids (Y=OH) of formula (I) using methods known to those skilled in the art.

Compounds of formula (I) in which B is substituted by $=CR^6R^7$ may be prepared from the corresponding ketones using any standard procedure, for example by employing a Wittig reaction. Compounds of formula (I) in which B is substituted by $=NOR^7$ may also be prepared from the corresponding ketones using any standard procedures known to those skilled in the art, for example by reacting the ketone with a hydroxylamine of formula $H_2NOR^7$ (XII). Hydroxylamines for formula (XII) may be commercially available, or may be prepared using standard conditions known to those skilled. in the art.

Similarly, intermediates of any appropriate formula may be. prepared by the interconversion of other compounds of the same formula. Thus, for example, a compound of formula (I) where $R^2$ is not H may be prepared from a compound of formula (I) where $R^2$ is H by reaction with a compound $R^2Z$ (where Z is as defined above) in the presence of a strong base such as lithiumdiisopropyalmide in an inert solvent such as tetrahydrofuran.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to the stromelysin, collagenase gelatinase, ADAM and ADAM-TS enzymes. Compounds according to the invention may also exhibit in vitro inhibition of membrane shedding events known to be mediated by metalloproteinases, for example, (α-APP, ACE, TGFα, TNF-α, Fas ligand, selecting, TNFR-I, TNFR-II, CD30, Il-6R, CD43, CD44, CD16-I, CD 16-II, Folate receptor, CD23, or IL-IRII.

The activity and selectivity of the compounds may be determined by use of the appropriate enzyme inhibition test, for example as described in Examples A-M of WO-A-9805635, by the assay for the inhibition of CD23 shedding described in WO-A-9924399, or by the following assay of TNF RI shedding.

The potency of the compounds of general formula (I) to act as inhibitors of the production of TNF RI is determined using the following procedure. A 100 μM solution of the inhibitor being tested or dilutions thereof is incubated at 37° C. in an atmosphere of 5% $CO_2$ with peripheral blood mononuclear cells (PBMC). PBMC are isolated from buffy coats by standard procedures using Ficoll. A 100μM solution of the inhibitor being tested or dilutions thereof is incubated for 22 hours at 37° C. in an atmosphere of 5% $CO_2$ with $1\times10^6$/ml PBMC stimulated with LPS. The cells are centrifuged down and the supernatant is assayed for TNF RI using a commercially available ELISA kit (R & D Systems). The activity in the presence of 0.1 mM inhibitor or dilutions thereof is compared to activity in a control devoid of inhibitor and results reported as that inhibitor concentration effecting 50% inhibition of the production of TNF RI.

This invention also relates to a method of treatment for patients (including man and/or mammalian animals raised in the dairy, meat or fur industries or as pets) suffering from disorders or diseases which can be attributed to stromelysin as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNF and MMPs. Accordingly in another aspect, this invention concerns:

a method of management (by which is meant treatment of prophylaxis) of disease or conditions mediated by TNF and/or MMPs in mammals, in particular in humans, which method comprises administering to the mammal an effective, amount of a compound of formula (I) above, or a pharmaceutically acceptable salt thereof, and a compound of formula (I) for use in human or veterinary medicine, particularly in the management (by which is meant treatment or prophylaxis) of diseases or conditions mediated by TNF and/or MMPs; and the use of a compound of formula (I) in the preparation of an agent for the management (by which is meant treatment or prophylaxis) of diseases or conditions mediated by TNF and/or MMPs.

The disease or conditions referred to above include inflammatory diseases, autoimmune diseases, cancer, cardiovascular diseases, diseases involving tissue breakdown such as rheumatoid arthritis, osteoarthritis, osteoporosis, neurodegeneration, Alzheimer's disease, stroke, vasculitis, Crohn's disease, ulcerative colitis, multiple sclerosis, periodontitis, gingivitis and those involving tissue breakdown such as bone resorption, haemorrhage, coagulation, acute phase response, cachexia and anorexia, acute infections, bacterial infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema, anaphylaxis, restenosis, congestive heart failure, endometriosis, atherosclerosis, endosclerosis, aspirin-independent anti-thrombosis, systemic lupus erythematosus and solid organ transplant.

Compounds of formula (I) may also be useful in the treatment of pelvic inflammatory disease (PID), age-related macular degeneration and cancer-induced bone resorption. Further, they can be used in the treatment of lung diseases, e.g. selected from cystic fibrosis, adult respiratory distress syndrome (ARDS), emphysema, bronchitis obliterans-organising pneumonia (BOOP), idiopathic pulmonary fibrosis (PIF), diffuse alveolar damage, pulmonary Langerhan's cell granulamatosis, pulmonary lymphangioleiomyomatosis (LAM) and chronic obstructive pulmonary disease (COPD). For the treatment of rheumatoid arthritis, osteoarthritis, and in diseases and indications resulting from the overexpression of matrix metalloendoproteinases such as found in certain metastatic tumour cell lines or other diseases mediated by the matrix metalloendoproteinases or increased TNF production, the compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated by the techniques described in U.S. Pat. No. 4256108, U.S. Pat. No. 4166452 and U.S. Pat. No. 4265874, to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the. active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethyleneoxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. For the purposes of this specification, topical application includes mouthwashes and gargles.

Dosage levels of the order of from about 0.05 mg to about 140 mg per kilogram of body weight per day are useful in the treatment of the above- indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day).

The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following Examples illustrate the invention.

INTERMEDIATE 1

6-Azaspiro[4,5]decane

Tetramethyleneglutarimide (2g) was added dropwise to a cooled solution of lithium aluminium hydride (182 g) in tetrahydrofuran (100 ml). The reaction was refluxed for 48 hrs, before being allowed to cool and quenched by the addition of water (1.8 ml), aqueous sodium hydroxide (15%, 1.8 ml), and water (5.4 ml). The precipitates were removed by filtration, and the filtrate collected. The solvent was removed in vacuo to yield the title compound as a yellow oil (1.63 g). MS, M+1 found 140

INTERMEDIATE 2

2 (6-Azaspiro[4,5]decane-8-sulfonylmethyl)-3-methylbutyric acid tert-butyl ester To a stirred solution of 2-chlorosulfonylmethyl-3-methyl-butyric acid tert-butyl ester (0.5 g) (WO-A-9805635) in dichloromethane (20 ml) at 0° C. was added triethylamine (0.52 ml), followed by Intermediate 1 (0.28 g). The reaction was allowed to warm to RT and stirred for 19 hrs, before the dichloromethane was removed in vacuo and the resulting slurry taken up in ethyl acetate (50 ml). The reaction was washed with aqueous citric acid (5%, 50 ml), aqueous sodium bicarbonate (saturated, 50 ml), brine (50 ml), and dried over magnesium sulphate (4 g). After filtration the solvent was removed in vacuo to yield the title compound as a yellow oil (75 mg). $R_f$ 0.72 (5% methanol in dichloromethane).

The following were prepared in the same manner

INTERMEDIATE 3

2-(1,4-Dioxa-8-azaspiro[4.5]decane-8-sulfonylmethyl)-3-methyl-butyric acid tert-butyl ester 2-Chlorosulfonylmethyl-3-methylbutyric acid tert-butyl ester, dichloromethane (60 ml), triethylamine (82 ml), and 1,4-dioxa-8-aza-spiro[4.5]decane(1.59 g) were reacted as above. Purification by flash chromatography (eluent 50% hexane/diethyl ether) yielded the title compound as a green gum (1.57 g). $R_f$ 0.35 (50% hexane/diethyl ether).

INTERMEDIATE 4

3-Methyl-2-(4-oxopiperidine-1-sulfonylmethyl) butyric acid tert-butyl ester Intermediate 3 (0.2 g) was taken up in acetone (20 ml) and water (95 ml) and tosic acid (0.02 g) was added. The reaction was refluxed for 48 hrs, before being allowed to cool. The acetone was removed in vacuo, and the resulting slurry taken up in ethyl acetate (40 ml) and washed with aqueous sodium bicarbonate (saturated, 25 ml) and brine (25 ml), and dried over magnesium sulphate (2 g). After filtration the solvent was removed in vacuo to yield the title compound as a yellow oil (0.16 g). $R_f$ 0.32 (30% hexane/diethyl ether).

INTERMEDIATE 5

2[4-(4-Chlorobenzylidene)piperidine-1-sulfonylmethyl]-3-methyl-butyric acid tert-butyl ester To a vigorously stirred solution of Intermediate 4 (0.18 g) and 4-chlorobenzyltriphenylphosphonium chloride (0.46 g) in dichloromethane (5 ml) was added aqueous sodium hydroxide (47%, 0.3 ml). After 4 hrs water (10 ml) was added and the reaction extracted with dichloromethane (2×10 ml). The combined organic phases were washed with water (10 ml), dried over magnesium sulphate (2 g), and the solvent removed in vacuo. The residue was purified by flash chromatography (eluent 70% hexane/diethyl ether) to yield the title compound as a colourless oil (0.07 g). $R_f$ 0.38 (70% hexane/diethyl ether).

EXAMPLE 1

2-(6-Azaspiro[4,5]decane-8-sulfonylmethyl)-3-methylbutyric acid

To a stirred solution of Intermediate 2 (757 mg) in dichloromethane (40 ml) was added trifluoroacetic acid (10 ml). After the reaction had stirred for 18 hrs at RT the solvent was removed in vacuo, and the reaction was azeotroped with hexane three times. The reaction was taken up in ethyl acetate (40 ml) and extracted with sodium hydroxide (1M, 2×30 ml). The combined aqueous washes were acidified to pH 4 with hydrochloric acid (3M), and extracted with dichloromethane (3×30 ml). The combined dichloromethane extracts were dried over magnesium sulphate (2 g), and the solvent removed in vacuo to yield the title compound as a white solid (357 mg). $R_f$ 0.38 (5% methanol in dichloromethane), MS, M+1 found 318.

The compound of Example 2 was prepared in a similar manner.

EXAMPLE 2

2-[4-(4-Chlorobenzylidene)piperidine-1-sulfonylmethyl]-3+methyl-butyric acid Intermediate 5 (67 mg), dichloromethane (10 ml) and trifluoroacetic acid (2 ml) were reacted as above for 5 hrs at RT. After similar workup the reaction yielded the title compound as a white solid (51 mg). $R_f$ 0.34 (30% hexane/diethyl ether), MS, M+1 found 386,388.

EXAMPLE 3

2-(6-Azaspiro[4,5]decane-8-sulfonylmethyl)-3-methylbutyric acid N-hydroxyamide To a stirred solution of Example 1 (300 mg) in dichloromethane (20 ml) and dimethylformamide(1 drop) was added oxalyl chloride (0.17 ml). The reaction was stirred at RT for 2 hrs, before being reduced in vacuo. The reaction was taken up in tetrahydrofuran (5 ml), and aqueous hydroxylamine (0.3 ml) was added. After 1 hour water (10 ml) was added, and the tetrahydrofuran removed in vacuo. The slurry was triturated with water (30 ml). The cream solid was collected by filtration, and dried in vacuo, to yield the title compound as a white solid (253 mg). $R_f$ 0.17 (5% methanol in dicyhloromethane), MS, M+1 found 333.

EXAMPLE 4

2-[4-(4-Chlorobenzylidene)piperidine-1-sulfonylmethyl]-3-methylbutyric acid N-hydroxyamide To a stirred solution of Example 2 (40 mg) in dichloromethane (20 ml) and dimethylformamide (1 drop) was added oxalyl chloride (0.021 ml). The reaction was stirred at RT for 4 hrs, before being reduced in vacuo. The reaction was taken up in tetrahydrofuran (5 ml), and aqueous hydroxylamine (0.1 ml) was added. After 15 minutes, water (10 ml) was added, and the tetrahydrofuran removed in vacuo. The slurry was extracted with ethyl acetate (40 ml), and washed with sodium bicarbonate (saturated, 20ml) and brine (20 ml), and dried over magnesium sulphate (1 g). After filtration the solvent was removed in vacuo to yield the title compound as a beige solid (41 mg). $R_f$ 0.33 (5% methanol in dichloromethane), Ms, M+1 found 401, 403.

What is claimed is:

1. A compound of formula (I)

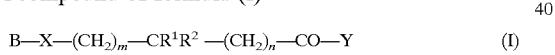

$$B-X-(CH_2)_m-CR^1R^2-(CH_2)_n-CO-Y \quad (I)$$

wherein m+n=1;

X is $SO_2$;

Y is NHOH;

$R^1$ is H, $R^x$ or a group (optionally substituted with $R^x$) selected from $C_{1-6}$ alkyl, $C_{2-6}$ alkenyl, $C_{2-6}$ alkyl, aryl, $C_{1-6}$ alkyl-aryl, heteroaryl, $C_{1-6}$ alkyl-heteroaryl, cycloalkyl, $C_{1-6}$ alkyl-cycloalkyl, heterocycloalkyl or $C_{1-6}$ alkyl-heterocycloalkyl; and $R^2$ is H or $C_{1-6}$ alkyl; or $CR^1R^2$ is cycloalkyl or heterocycloalkyl optionally substituted with $R^x$;

$R^x$ is $R^3$ or a group (optionally substituted with $R^3$) selected from $C_{1-6}$ alkyl, aryl, $C_{1-6}$ alkyl-aryl, heteroaryl or $C_{1-6}$ alkyl-heteroaryl;

$R^3$ is $OR^7$, $OCF_3$, $OCH_2F$, $OCHF_2$, $COR^7$, $CO_2R^4$, $CON(R^7)_2$, $N(R^7)_2$, $NR^7COR^7$, $NR^7CON(R^7)_2$, $NR^7CO_2R^8$, $NR^7SO_2R^8$, $S(O)_{0-2}R^8$, $SO_2N(R^7)_2$, cycloimidyl (optionally substituted with $R^5$) or, where $R^3$ is not attached to an aryl or heteroaryl group, $R^3$ may also be =O, =$NOR^{10}$ or =NOH;

$R^4$ is H or $C_{1-6}$ alkyl;

$R^5$ is $C_{1-6}$ alkyl;

B is cycloalkyl or cycloalkenyl substituted with a group selected from =O, =$NOR^7$ or =$CR^6R^7$, B is heterocycloalkyl or heterocycloalkenyl substituted with =$CR^6R^7$, or B is a spirocyclic system optionally substituted by $R^3$ or $R^7$;

$R^6$ is H or $C_{1-6}$ alkyl;

$R^7$ is H or a group selected from $C_{1-6}$ alkyl, aryl, $C_{1-6}$ alkyl-aryl, heteroaryl, $C_{1-6}$ alkyl-heteroaryl, cycloalkyl, $C_{1-6}$ alkyl-cycloalkyl, heterocycloalkyl or $C_{1-6}$ alkyl-heterocycloalkyl, wherein said group is optionally substituted with $R^8$, $COR^8$, $SO_{0-2}R_8$, $CO_2R^8$, $OR^8$, $OCF_3$, $OCH_2F$, $OCHF_2$, $CONR^4R^8$, $NR^6R^8$ or $SO_2NR^4R^8$ and for each case of $N(R^7)_2$ the $R^7$ groups are the same or different, or $N(R^7)_2$ is heterocycloalkyl optionally substituted with $R^8$, $COR^8$, $SO_{0-2}R^8$, $CO_2R^8$, $OR^8$, $CONR^4R^8$, $NR^4R^8$, or $SO_2NR^4R^8$; and $R^8$ is $C_{1-6}$ alkyl, aryl, $C_{1-6}$ alkyl-aryl heteroaryl or $C_{1-6}$ alkyl-heteroaryl;

or the salt, solvate, hydrate, N-oxide, protected amino, protected carboxy or protected hydroxamic acid derivative thereof, or the enantiomeric, diastereomeric, or racemic mixture thereof.

2. The compound according to claim 1, wherein B is heterocycloalkyl or heterocycloalkenyl bound through N to X.

3. A compound according to claim 1 wherein $R^1$ is H, $R^3$ or a group (optionally substituted with $R^3$) selected from $C_{1-6}$ alkyl, $C_{2-6}$ alkenyl, $C_{2-6}$ alkenyl, aryl, $C_{1-6}$alkyl-aryl, heteroaryl, $C_{1-6}$ alkyl-heteroaryl, cycloalkyl, $C_{1-6}$alkyl-cycloalkyl, heterocycloalkyl and $C_{1-6}$ alkyl-heterocycloalkyl;

$R^2$ is H or $C_{1-6}$ alkyl;

or $CR^1R^2$ is cycloalkyl or heterocycloalkyl optionally substituted with $R^3$ or a group (optionally substituted with $R^3$) selected from $C_{1-6}$ alkyl, aryl, $C_{1-6}$ alkyl-aryl, heteroaryl and $C_{1-6}$ alkyl-heteroaryl; and $R^3$ is $OR^7$, $COR^7$, $CO_2R^4$, $CON(R^7)_2$, $NR^7COR^7$, $NR^7CON(R^7)_2$, $NR^7CO_2R^8$, $NR^7SO_2R^8$, $S(O)_{0-2}R^8$, $SO_2N(R^7)_2$ or cycloimidyl (optionally substituted with $R^5$).

4. The compound according to claim 1, which is 2-(6-Azaspiro[4,5]decane-8-sulfonylmethyl)-3-methylbutyric acid N-hydroxyamide or 2-[4(4Chlorobenzylidene)piperidine-1-sulfonylmethyl]-3-methylbutyric acid N-hydroxyamide.

5. A compound of according to claim 1 which is chiral and in the form of a single enantiomer or diastereomer.

6. A pharmaceutical composition, comprising a compound of claim 1, and a pharmaceutically acceptable diluent or carrier.

7. A compound which is 2-(6-Azaspiro[4,5]decane-8-sulfonylmethyl)-3-methylbutyric acid.

8. A compound which is 2-[4-(4-Chlorobenzylidene)piperidine-1-sulfonylmethyl]-3-methylbutyric acid.

* * * * *

UNITED STATES PATENT AND TRADEMARK OFFICE
CERTIFICATE OF CORRECTION

PATENT NO. : 6,506,764 B1  Page 1 of 1
DATED : January 14, 2003
INVENTOR(S) : Andrew Douglas Baxter et al.

It is certified that error appears in the above-identified patent and that said Letters Patent is hereby corrected as shown below:

Column 11,
Line 48, "$C_{2-6}$ alkyl" should read -- $C_{2-6}$ alkynyl --.

Column 12,
Line 27, "or the enantiomeric, diastereomeric," should read -- or the enantiomer, diastereomer --.
Line 31, "A compound" should read -- The compound --.
Line 33, "$C_{2-6}$ alkenyl, $C_{2-6}$ alkenyl, aryl" should read -- $C_{2-6}$ alkenyl, $C_{2-6}$ alkynyl, aryl --.
Line 35, "heterocycloalkyl and" should read -- heterocycloalkyl or --.
Lines 35-36, "alkyl-heterocycloalkyl" should read -- alkyl-heterocycloalkyl; and --.
Line 41, "heteroaryl and" should read -- heteroaryl or --.
Line 42, "$CON(R^7)_2$, $NR^7COR^7$," should read -- $CON(R^7)_2$, $N(R^7)_2$, $NR^7COR^7$, --.
Lines 49-50, "2-[4(4Chlorobenzylidene)piperidine-1-sulfonylmethyl]-3-methylbutyric acid N-hydroxyamide." should read -- 2-[4-(4-Chlorobenzylidene)piperidine-1-sulfonylmethyl]-3-methylbutyric acid N-hydroxyamide. --.

Signed and Sealed this

Tenth Day of June, 2003

JAMES E. ROGAN
*Director of the United States Patent and Trademark Office*